United States Patent [19]

Kyuko et al.

[11] Patent Number: 5,396,007
[45] Date of Patent: Mar. 7, 1995

[54] PROCESS FOR PRODUCTION OF DIMETHYLNAPHTHALENE

[75] Inventors: Yoichi Kyuko; Shinji Ozawa; Makoto Takagawa; Kenji Inamasa, all of Tsukuba, Japan

[73] Assignee: Mitsubishi Gas Chemical Company, Inc., Tokyo, Japan

[21] Appl. No.: 86,506

[22] Filed: Jul. 1, 1993

[30] Foreign Application Priority Data

Aug. 31, 1992 [JP] Japan .................. 4-231892

[51] Int. Cl.$^6$ ................................. C07C 5/00
[52] U.S. Cl. ................... 585/400; 585/654; 585/658; 585/660
[58] Field of Search ............... 585/400, 440, 444, 660, 585/658, 654

[56] References Cited

U.S. PATENT DOCUMENTS

| | | | |
|---|---|---|---|
| 3,781,375 | 12/1973 | Shima | 260/668 D |
| 4,999,326 | 3/1991 | Sikkenga | 502/30 |
| 5,012,024 | 4/1991 | Sikkenga et al. | 585/320 |
| 5,189,234 | 2/1993 | Amelse | 585/320 |

Primary Examiner—Asok Pal
Assistant Examiner—P. Achutamurthy
Attorney, Agent, or Firm—Frishauf, Holtz, Goodman & Woodward

[57] ABSTRACT

A process for producing dimethylnaphthalene by the dehydrogenation of dimethyl-tetrahydronaphthalene which comprises carrying out the dehydrogenation reaction in a gaseous state at a temperature of 200° to 350° C. in the presence of a diluting medium and by the use of a platinum and/or palladium catalyst supported on an activated carbon carrier. The process is capable of producing industrially useful dimethylnaphthalene with a high yield and a high selectivity and minimized side reactions, over a long stabilized period.

20 Claims, No Drawings

PROCESS FOR PRODUCTION OF DIMETHYLNAPHTHALENE

BACKGROUND OF THE INVENTION

1. Field of the Invention

The present invention relates to a process for producing dimethylnaphthalene (hereinafter sometimes abbreviated to "DMN"). More particularly, it pertains to a process for efficiently producing DMN with high yield and high selectivity over a long stabilized period by the dehydrogenation of dimethyl-tetrahydronaphthalene (hereinafter sometimes abbreviated to "DMTHN") under specific reaction conditions by the use of a specific catalyst.

DMN has numerous uses as a raw material for a high molecular material, such as a pharmaceutical material or the like. For example, 1,5-DMN which is obtained by the dehydrogenation of 1,5-DMTHN can be converted into industrially useful 2,6-naphthalene-dicarboxylic acid through the steps of isomerization and oxidation.

2. Description of the Related Arts

The process for dehydrogenating a tetrahydronaphthalene series compound into a naphthalene series compound in a liquid phase by the use of a noble metal catalyst supported on a powdery carrier has been known since long years before as a process for synthesizing a substituted naphthalene series compound.

For example, Eberhardt et al. discloses in J. Org. Chem., vol. 30 (1965), pp 82 to 84, a process for producing 1,5-, 1,7- or 1,4-DMN by dehydrogenating 1,5-, 1,7- or 1,4-DMTHN, respectively in liquid phase by the use of a palladium catalyst supported on a powdery activated carbon.

In addition, Japanese Patent Application Laid-Open No. 500052/1991 through PCT and U.S. Pat. No. 5,012,024 disclose the same process as above using a similar catalyst, except that the equilibrium conditions are brought to the advantageous side for DMN by continuously removing the hydrogen generated in the reaction system.

Moreover, U.S. Pat. No. 4,999,326 discloses the same process as above using a similar catalyst, which process includes a method of activating the catalyst deteriorated in reaction activity after reaction.

On the other hand, there is also known the process for dehydrogenating DMTHN into DMN in a gas phase as exemplified hereunder.

Japanese Patent Application Publication No. 30616/1975 and U.S. Pat. No. 3,781,375 disclose the use of a chromia/alumina catalyst in a gas-phase reaction.

In addition, Japanese Patent Application Laid-Open No. 67261/1973 discloses the use of rhenium or palladium catalyst supported on alumina in a gas-phase dehydrogenation of DMTHN.

Furthermore, Japanese Patent Application Publication No. 27694/1985 discloses a process for dehydrogenating DMTHN in a stream of hydrogen gas by the use of platinum catalyst supported on alumina.

Among the publicly known processes as mentioned above, the process for dehydrogenating DMTHN into DMN in a liquid phase by the use of a noble metal catalyst supported on a powdery carrier suffers the disadvantages that a long period is required for the completion of the reaction and the catalyst in fine powder form makes it extremely troublesome to separate the produced DMN from the catalyst. The process using a palladium catalyst supported on powdery activated carbon in the dehydrogenation in a liquid phase can not be said to be an industrially satisfactory process, since the process necessitates frequent regeneration of the catalyst repeatedly because of remarkable deterioration of catalyst activity as is revealed in U.S. Pat. No. 4,999,326.

On the other hand, the process for dehydrogenating DMTHN into DMN in a gas phase by the use of chromia/alumina catalyst or rhenium or palladium catalyst supported on alumina and the process for dehydrogenating DMTHN into DMN in a stream of hydrogen gas by the use of a platinum catalyst supported on alumina require a high reaction temperature in the range of 350° to 450° C. in order that a sufficient reaction rate may be maintained. Due to the high reaction temperatures, the above-mentioned processes suffer the drawbacks that the processes are liable to cause side reactions such as isomerization and demethylation of the methyl groups in DMN in the course of the reaction, and DMTHN and DMN tend to polymerize to form cokes on the catalyst, whereby the catalyst activity is subject to deterioration. Furthermore, the dehydrogenation of DMTHN into DMN is a marked endothermic reaction and therefore, the high reaction temperatures required in the aforesaid processes raised a serious problem regarding a heating system in the industrial reaction equipment. Specifically, it is impossible to adopt therein the heating system by the use of a multi-tube isothermal reactor using a heating medium oil which system is usually applied to an endothermic reaction at a relatively low temperature. Furthermore, an attempt to adopt therein an adiabatic reaction system that is widely employed for an endothermic reaction at a higher temperature necessitates the heating of DMTHN to a temperature much higher than the actually necessary reaction temperature to introduce it in the catalyst layer, which attempt unfavorably brings about remarkable side reactions such as isomerization and demethylation of the methyl groups in DMN.

As described hereinbefore, any of the aforestated conventional processes for dehydrogenating DMTHN into DMN can not render itself an industrially available process because of the serious defect remaining unsolved at the present time.

SUMMARY OF THE INVENTION

It is an object of the present invention to develop and provide a process capable of producing DMN with high yield and high selectivity by dehydrogenating DMTHN into DMN at a lower reaction temperature and at the same time, of maintaining a long-term stabilized reaction.

Under such circumstances, intensive research and investigation were made by the present inventors on the development of an excellent process for producing DMN by efficiently dehydrogenating DMTHN into DMN by overcoming the aforestated problems. As a result, it has been found by the present inventors that it is possible to proceed with the dehydrogenation reaction almost quantitatively at a lower temperature less than 350° C. while suppressing unfavorable side reactions such as demethylation, dealkylation, disproportionation and isomerization by carrying out the reaction in a gas phase in the presence of a diluting medium by the use of a platinum and/or palladium catalyst supported on activated carbon and that the reaction can be continued with high catalyst activity and high yield of DMN for a long period of several thousands hours. The present invention has been accomplished on the basis of the above-mentioned finding.

Specifically, the present invention provides a process for producing dimethylnaphthalene (DMN) by dehydrogenating dimethyl-tetrahydronaphthalene (DMTHN) which comprises effecting the dehydrogenation reaction in a gaseous state at a temperature in the range of 200° to 350° C. in the presence of a diluting medium by the use of at least one metallic catalyst selected from platinum and palladium, said catalyst being supported on activated carbon.

DESCRIPTION OF PREFERRED EMBODIMENTS

Among a large number of DMTHN isomers, all the DMTHN excluding 1,1-DMTHN and 2,2-DMTHN may be employed for the purpose of the present invention. 1,1-DMTHN and 2,2-DMTHN in which two methyl groups are bonded to the same carbon atom can not be used in the process of the present invention since they are not converted into DMN by dehydrogenation.

The DMTHN can be produced by any of various processes, which are exemplified, as an industrially significant process, by the process disclosed by Eberhardt et al. in J. Org. Chem., vol. 30 (1965), pp 82 to 84, wherein an alkylbenzene series compound is subjected to addition reaction with 1,3-butadiene by using an alkali metal catalyst and the produced alkenylbenzene series compound is cyclized into DMTHN by the use of an acid catalyst. In the above-mentioned process, for example, 1,5-DMTHN is produced from o-xylene and 1,3-butadiene via 5-(o-tolyl)-2-pentene; 1,7-DMTHN is produced from p-xylene and 1,3-butadiene via 5-(p-tolyl)-2-pentene; 1,4-DMTHN from ethylbenzene via 5-phenyl-2-hexene; and 5-(m-tolyl)-2-pentene that is produced from m-xylene and 1,3-butadiene can be cyclized into the mixture of 1,6-DMTHN and 1,8-DMTHN.

In addition, DMTHN can be produced by partial hydrogenation of DMN. The aforementioned process is not a process of creating a new DMN skelton, but it is significant as a process for isomerizing DMN by transferring methyl groups thereof. It is known that DMN has 10 isomers according to the positions of methyl groups, which are classified into the under-mentioned 4 groups Group A—1,5-DMN; 1,6-DMN; and 2,6-DMN
Group B—1,7-DMN; 1,8-DMN; and 2,7-DMN
Group C—1,3-DMN; 1,4-DMN; and 2,3-DMN
Group D—1,2-DMN and that the isomerization in the same group (intragroup isomerization) is relatively easy, whereas that among different groups (intergroup isomerization) is extremely difficult because of the forbidance derived from the resonance constitution of naphthalene rings. For example, in the case of isomerizing DMN in Group B to that in Group A, the reaction rate is unreasonably low and side reactions such as demethylation substantially take place, thereby failing to attain a favorable result, even if the reactants are brought into direct contact with an isomerization catalyst. In view of above, there is proposed a method of facilitating an intergroup isomerization by partially hydrogenating DMN in Group B into DMTHN to eliminate the forbidance and isomerizing the resultant DMTHN under the non-forbidance condition, followed by dehydrogenation into the objective DMN. (Refer to Japanese Patent Application Laid-Open Nos. 76853/1973 and 96569/1973, etc.) The process according to the present invention is applicable to the dehydrogenation step in the above-mentioned intergroup isomerization method without any problem, thereby enabling favorable reaction performance and sufficient life of the catalyst.

The process for producing DMTHN is not limited to the aforestated process but may be exemplified by various available processes.

There is employed a platinum and/or palladium catalyst supported on activated carbon in the process according to the present invention.

Although as the carrier of the platinum or palladium catalyst for general dehydrogenation reaction, alumina, silica or the like other than activated carbon according to the present invention is widely used on an industrial scale, only activated carbon is favorably used as the carrier of the catalyst in the process of the present invention.

A platinum or palladium catalyst supported on alumina is inferior to the same catalyst supported on activated carbon according to the present invention with regard to catalyst activity itself and change in the activity with the lapse of time. In order to enhance the catalytic activity of the catalyst supported on alumina, it is necessary to carry out the reaction at a temperature as high as 350° to 450° C., which however is unfavorable since side reactions such as isomerization and/or demethylation of DMTHN as the starting raw material and the produced DMN take place due to direct contact with the acidic carrier at an elevated temperature. A platinum or palladium catalyst supported on silica suffers from the disadvantage as is the case with the same catalyst supported on alumina.

Moreover, even if the palladium or platinum catalyst according to the present invention is replaced with a noble metal catalyst usually exhibiting activity in dehydrogenation reaction such as ruthenium or rhenium supported on activated carbon, the catalytic activity thereof is unfavorably much lower than that of the present invention.

As for the reaction in the process according to the present invention, the use of platinum and/or palladium catalyst supported on activated carbon is the only way of enabling DMN to be produced by dehydrogenating DMTHN with high yield and high selectivity at a low temperature region of 350° C. and lower over a long-term stabilized period.

The platinum or palladium catalyst supported on activated carbon to be used as the catalyst in the process of the present invention has been industrially employed since many years before and can be produced by a conventional process. The activated carbon to be used as the catalyst carrier in the process of the present invention is available from that in any of various types including crushed, molded or powdered activated carbon each of plant or mineral origin.

The amount of the platinum or palladium catalyst to be supported on activated-carbon carrier is 0.05% to 15%, preferably 0.1% to 10% by weight based on the carrier. An amount thereof less than 0.05% by weight exerts catalytic activity to some extent but is industrially impractical because of low reaction rate, whereas that more than 15% by weight is acceptable but not recommendable because of its causing expensiveness.

The platinum or palladium catalyst is usually used alone but may be used in combination with the other, or with a metallic component other than platinum and palladium provided that the amount thereof is within an allowable limit.

The dehydrogenation reaction of DMTHN into DMN in the present invention is put into practice in the presence of a diluting medium under the conditions in which both DMTHN as the starting raw material and DMN as the objective product are present substantially in a gas phase.

The dehydrogenation reaction can be caused by bringing DMTHN in a liquid phase into contact with the platinum or palladium catalyst supported on activated carbon, but the aforementioned liquid-phase reaction is unfavorable by reason of decrease in reaction rate as well as deterioration of catalytic activity with the elapse of time.

As opposed to the liquid phase reaction, the gas-phase reaction in the presence of a diluting medium as described hereinbefore is capable of remarkably enhancing the rate of reaction with minimized side reactions and maintaining the objective reaction with high yield over a long stabilized period. The present invention is founded on the above-mentioned finding.

Examples of the usable diluting medium in the present invention include an inert gas such as nitrogen, argon and helium, aliphatic hydrocarbons and aromatic hydrocarbons each assuming a gaseous state under the reaction conditions and the like. The diluting medium may be used alone or in combination with at least one other diluting medium.

The aliphatic hydrocarbon to be used is that which assumes a gaseous state under the reaction conditions and preferably has a boiling point lower than that of the objective DMN. Specific examples thereof include a linear or branched paraffin having 1 to 15 carbon atoms and, as the particularly desirable one, a linear or branched paraffin having 6 to 10 carbon atoms which is easily separated from the products including hydrogen and DMN.

The aromatic hydrocarbon to be used is that which assumes a gaseous state under the reaction conditions, a particularly desirable aromatic hydrocarbon is one in the form of a liquid at room temperature having a boiling point lower than that of the objective DMN. Specific examples thereof include benzene, toluene, o-xylene, m-xylene, p-xylene, ethylbenzene, pseudocumene, mesitylene, n-propylbenzene and cumene.

The amount of the diluting medium to be used in the process according to the present invention is 0.1 to 100, preferably 0.5 to 20 in molar ratio based on DMTHN as the starting raw material.

Examples of the reaction method applicable to the implementation of the reaction according to the present invention include a fixed-bed system, a moving-bed system, a fluidized-bed system, etc., each being capable of bringing the starting raw material in a gaseous state into contact with the catalyst. Among them particularly desirable is the fixed-bed tubular reaction system having the catalyst packed therein and passing through the starting raw material.

The dehydrogenation reaction in the process according to the present invention is carried out at a reaction temperature in the range of 200° to 350° C., preferably 240° to 300° C. The reaction temperature in the above range is suitable for enabling a heating medium oil to be used for heating and for constituting an extremely practical process from the viewpoint of industrial operation.

A reaction temperature higher than 350° C., unfavorably causes marked side reactions such as dealkylation, isomerization and polymerization each of DMTHN and/or DMN and at the same time, remarkable deterioration of the activity of the catalyst. The acceleration of side reactions at elevated temperatures is due to various unfavorable reactions at high temperatures caused by platinum or palladium each as an active metal as well as a variety of side reactions at high temperatures brought about by the activated carbon used as the carrier. It has previously been known that activated carbon has various surface functional groups and functions at elevated temperatures as a catalyst for reaction such as dealkylation and dehydrogenation of hydrocarbons.

On the other hand, a reaction temperature lower than 200° C. is also unfavorable because of incapability of assuring a sufficient rate of reaction.

The reaction pressure in the process according to the present invention is 0.1 to 10 atm, preferably 0.5 to 3 atm in terms of absolute pressure. The reaction temperature together with reaction pressure are selected within the above-mentioned ranges so that DMTHN as the starting raw material and the objective DMN are present in gas phase in the presence of the diluting medium.

The feed rate of DMTHN as the starting raw material is 0.1 to 10, preferably 0.2 to 5 times by weight per hour based on the unit weight of the catalyst.

In summary, the process according to the present invention enables industrial production of industrially useful DMN with high yield and high selectivity by the dehydrogenation of DMTHN over a long stabilized period, thereby rendering itself highly significant from the industrial point of view.

In what follows, the present invention will be described in more detail with reference to the examples and comparative examples, which examples shall not be construed to limit the present invention thereto.

Since the formation of a low-boiling light component and a high-boiling heavy component due to the present hydrogenation reaction was hardly recognized, the conversion efficiency, yield and selectivity were determined from the compositions of the starting raw liquid and the product liquid using the following respective formulae on the basis of the assumption that the number of moles remained unchanged throughout the reaction:

Cnversion efficiency of DMTHN $(\%) = [(a-b)/a] \times 100$

DMN yield $(\%) = [(c-d)/a] \times 100$

Selectivity to DMN $(\%) = (y/z) \times 100$ wherein "a" indicates a mol fraction of DMTHN in starting raw liquid, "b" indicates a mol fraction of DMTHN in product liquid, "c" indicates a mol fraction of DMN in product liquid, "d" indicates a mol fraction of DMN in starting raw liquid, "y" indicates a DMN yield (%) and "z" indicates a conversion efficiency of DMTHN (%).

EXAMPLE 1

A quartz glass-made tubular reactor with 13 mm inside diameter and 350 mm length was packed with 4.0 g of 1% platinum/activated-carbon catalyst that had been uniformized to 0.5 to 1.0 mm particle size (produced by NE CHEMCAT Corporation), and glass beads were filled on the catalyst bed in the reactor in 200 mm height. The reactor was heated to 280° C. and charged with a 32% solution of the starting raw liquid containing 1,5-dimethyltetralin as the principal component as shown in Table 1 in heptane from above the glass beads at a feed rate of 7.0 g/hour to proceed with the dehydrogenation reaction for continuous 2000 hours approximately. The reaction results in each time period of liquid feed are collectively given in Table 1.

EXAMPLE 2

The procedure in Example 1 was repeated to investigate the change in the activity of the catalyst except that 1% palladium/activated-carbon catalyst (produced by NE CHEMCAT Corporation) was employed in place of 1% platinum/activated-carbon catalyst and that the reaction temperatures were set to those as indicated in Table 2. The rection results are given in Table 2.

COMPARATIVE EXAMPLE 1

The procedure in Example 2 was repeated to investigate the activity of the catalyst except that 1% palladium/alumina catalyst (about 1 mm sphere, produced by NE CHEMCAT Corporation) was employed in place of 1% palladium/activated-carbon catalyst. The reaction results are given in Table 3. It can be seen from Table 3 that the use of palladium/alumina catalyst can attain the activities and reaction results in the initial stage comparable to those by the use of palladium supported on activated carbon but results in remarkable deterioration of the activities with the lapse of time and also that an elevated temperature up to a 400° C. leads to considerable decrease in selectivity to the objective DMN.

EXAMPLE 3

A stainless steel-made tubular reactor with 17 mm inside diameter and 300 mm length was packed with 10 g of 1% palladium/activated-carbon catalyst that had been uniformized to 1.0 to 2.63 mm particle size (produced by NE CHEMCAT Corporation) and was heated to 290° C., while allowing nitrogen to flow therein. Nitrogen gas at a rate of 20 cc/min. and the starting raw liquid having the composition in Table 4 at a rate of 10 g/hour were introduced into the reactor the inside of which was maintained at a pressure of 0.5 kg/cm²G to proceed with the reaction. Under the above-mentioned reaction conditions, all of the reaction liquid was vaporized, whereby the reaction was carried out in gas phase only. The reaction results are given in Table 4.

COMPARATIVE EXAMPLE 2

The procedure in Example 3 was repeated except that the reactor inside pressure was set to 5.0 kg/cm²G and the introduction of nitrogen gas was omitted to proceed with the rection in liquid phase instead of gas phase. The reaction results are given in Table 4 along with those of Example 3 for the purpose of comparison therebetween.

EXAMPLE 4

A pyrex glass-made tubular reactor with 8 mm inside diameter and 300 mm length was packed with 1.0 g of 0.5% platinum/activated-carbon catalyst that had been uniformized to 0.5 to 1.0 mm particle size (produced by NE CHEMCLAT Corporation), and α-alumina beads were filled on the catalyst bed in the reactor in 150 mm height. The reactor was heated to 280° C. and charged with a 32% solution of the starting raw liquid containing 1,5-dimethyltetralin as the principal component as shown in Table 5 in heptane from above the α-alumina beads at a feed rate of 1.56 g/hour to proceed with dehydrogenation reaction for continuous 1000 hours approximately. The reaction results in each time period of liquid feed are given in Table 5.

COMPARATIVE EXAMPLES 3 TO 4

The procedure in Example 4 was repeated to investigate the change in the activity of the catalyst expect that 0.5% platinum/alumina catalyst or 1% platinum/silica catalyst was employed in place of platinum/activated-carbon catalyst. The reaction results in each time period of liquid feed are given in Table 5.

TABLE 1

| Liquid feed time (hr) | 72 | 467 | 920 | 1568 | 2006 |
|---|---|---|---|---|---|
| Temperature (°C.) | 280 | 280 | 280 | 280 | 280 |
| Composition of starting material (%) | | | | | |
| 1,5-+1,8-DMTHN | 95.2 | 98.3 | 97.2 | 97.9 | 97.5 |
| 1,6-+1,7-DMTHN | 1.0 | 0.1 | 0.2 | 0.2 | 0.2 |
| 1,5-DMN | 0.3 | 0.3 | 0.1 | 0.2 | 0.3 |
| 1,6-DMN | 0.04 | — | — | — | — |
| low boiling light components | 3.5 | 1.3 | 2.5 | 1.7 | 2.0 |
| DMN yield (%) | | | | | |
| 1,5-DMN | 97.8 | 99.2 | 99.0 | 98.8 | 98.6 |
| 1,6-+1,7-DMN | 1.2 | 0.1 | 0.2 | 0.2 | 0.3 |
| 1,8-DMN | 0.3 | 0.2 | 0.3 | 0.3 | 0.4 |
| Conversion efficiency (%) | 99.5 | 99.6 | 99.5 | 99.3 | 99.3 |
| Selectivity to DMN (%) | 99.8 | 99.9 | 99.9 | 99.9 | 99.9 |

TABLE 2

| Liquid feed time (hr) | 44 | 646 | 1009 | 1509 | 2012 |
|---|---|---|---|---|---|
| Temperature (°C.) | 290 | 300 | 300 | 300 | 300 |
| Composition of starting material (%) | | | | | |
| 1,5-+1,8-DMTHN | 93.5 | 88.7 | 91.2 | 90.8 | 94.2 |
| 1,6-+1,7-DMTHN | 1.7 | 5.8 | 3.3 | 3.1 | 1.0 |
| 1,5-DMN | 1.0 | 1.6 | 0.6 | 0.4 | 0.9 |
| 1,6-DMN | 0.1 | 0.4 | 0.1 | 0.1 | 0.1 |
| low boiling light components | 3.7 | 3.5 | 4.8 | 5.5 | 3.8 |
| DMN yield (%) | | | | | |
| 1,5-DMN | 96.5 | 90.4 | 91.4 | 90.7 | 91.7 |
| 1,6-+1,7-DMN | 2.0 | 6.3 | 3.6 | 3.8 | 0.7 |
| 1,8-DMN | 0.4 | 0.5 | 0.5 | 0.4 | 0.5 |
| Conversion efficiency (%) | 98.9 | 97.3 | 95.5 | 95.0 | 93.0 |
| Selectivity to DMN (%) | 100 | 99.9 | 100 | 99.9 | 99.9 |

TABLE 3

Composition of starting material
1,5-+1,8-DMTHN 97.5%,
1,6-+1,7-DMTHN 0.9%
1,5-DMN 0.2%, 1,6-DMN 0%,
low boiling light components 1.4%

| Liquid feed time (hr) | 2 | 24 | 42 | 51 | 70 |
|---|---|---|---|---|---|
| Temperature (°C.) | 290 | 290 | 300 | 350 | 400 |
| DMN yield (%) | | | | | |
| 1,5-DMN | 98.3 | 88.0 | 70.7 | 32.7 | 26.5 |
| 1,6-+1,7-DMN | 1.0 | 0.9 | 0.5 | 1.2 | 2.8 |
| 1,8-DMN | 0.4 | 0.3 | 0.4 | 0.1 | 0.1 |
| Conversion efficiency (%) | 99.7 | 89.2 | 71.1 | 34.5 | 31.5 |
| Selectivity to DMN (%) | 100 | 100 | 100 | 98.5 | 93.1 |

TABLE 4

Composition of starting material
1,5-+1,8-DMTHN 91.6%,
1,6-+1,7-DMTHN 1.1%
1,5-DMN 1.7%, 1,6-DMN 0.1%,
low boiling light components 5.6%

| | Example 3 | Comparative Example 2 |
|---|---|---|
| Temperature (°C.) | 290 | 290 |
| Pressure (kg/cm² G) | 0.5 | 5.0 |
| fed N₂ amount (cc/min) | 20 | 0 |
| Reaction phase | gas phase | liquid phase |

TABLE 4-continued

Composition of starting material
1,5-+1,8-DMTHN 91.6%,
1,6-+1,7-DMTHN 1.1%
1,5-DMN 1.7%, 1,6-DMN 0.1%,
low boiling light components 5.6%

|  | Example 3 | Comparative Example 2 |
|---|---|---|
| Results during 11 hours of liquid feed DMN yield (%) |  |  |
| 1,5-DMN | 94.8 | 80.9 |
| 1,6-+1,7-DMN | 1.4 | 1.1 |
| 1,8-DMN | 0.3 | 0.3 |
| Conversion efficiency (%) | 96.7 | 82.7 |
| Selectivity to DMN (%) | 99.8 | 99.6 |

TABLE 5

Composition of starting material
1,5-+1,8-DMTHN 97.5%,
1,6-+1,7-DMTHN 0.9%,
1,5-DMN 0.2%,
1,6-DMN 0%, low boiling
light components 1.4%

|  | Example 4 | | | | Comparative Example 3 | | Comparative Example 4 | |
|---|---|---|---|---|---|---|---|---|
| Catalyst | 0.5% Pt/activated carbon | | | | 0.5% Pt/Al$_2$O$_3$ | | 0.5% Pt/SiO$_2$ | |
| Liquid feed time (hr) | 20 | 116 | 223 | 988 | 10 | 32 | 3 | 28 |
| Temperature (°C.) | 260 | 260 | 280 | 280 | 270 | 270 | 260 | 270 |
| DMN yield (%) | | | | | | | | |
| 1,5-DMN | 94.3 | 96.4 | 98.0 | 97.4 | 97.5 | 82.3 | 96.7 | 84.7 |
| 1,6-+1,7-DMN | 0.9 | 0.7 | 1.0 | 0.8 | 0.9 | 0.5 | 0.6 | 0.6 |
| 1,8-DMN | 0.3 | 0.3 | 0.2 | 0.2 | 0.3 | 0.2 | 0.2 | 0.2 |
| Conversion efficiency (%) | 95.6 | 97.6 | 99.3 | 98.4 | 98.7 | 83.0 | 97.7 | 85.6 |
| selectivity to DMN (%) | 99.9 | 99.8 | 99.9 | 99.9 | 99.9 | 100 | 99.8 | 99.9 |

EXAMPLE 5

The procedure in Example 4 was repeated except that a 2% solution of the starting raw liquid containing 1,5-dimethyltetralin as the principal component as shown in Table 6 in toluene was used in place of the solution of the same in heptane, and that the reaction was continued for about 2000 hours. The reaction results in each time period of liquid feed are given in Table 6.

TABLE 6

Composition of starting material
1,5-+1,8-DMTHN 97.2%,
1,6-+1,7-DMTHN 0.8%,
1,5-DMN 0.2%,
1,6-DMN 0%, low boiling
light components 1.8%

| Liquid feed time (hr) | 18 | 127 | 264 | 692 | 1008 | 2007 |
|---|---|---|---|---|---|---|
| Temperature (°C.) | 260 | 260 | 280 | 280 | 290 | 290 |
| DMN yield (%) | | | | | | |
| 1,5-DMN | 95.3 | 96.9 | 98.3 | 98.1 | 98.4 | 97.6 |
| 1,6-+1,7-DMN | 0.7 | 0.6 | 0.7 | 0.6 | 0.8 | 0.7 |
| 1,8-DMN | 0.2 | 0.1 | 0.2 | 0.1 | 0.1 | 0.1 |
| Conversion efficiency (%) | 96.2 | 97.6 | 99.2 | 98.8 | 99.4 | 98.5 |
| Selectivity to DMN (%) | 100 | 100 | 100 | 99.9 | 99.9 | 99.9 |

COMPARATIVE EXAMPLES 5 TO 6

The procedure in Example 1 was repeated to investigate the activity of the catalyst except that 1% rhenium-/activated-carbon catalyst was used in Comparative Example 5 and 1% ruthenium/activated-carbon catalyst was used in Comparative Example 6 each in place of 1% platinum/activated-carbon catalyst. The reaction results are given in Table 7. It can be seen from Table 7 that the activities are low as compared with the activity of any of platinum/activated-carbon catalyst and palladium/activated-carbon catalyst.

TABLE 7

Composition of starting material
1,5-+1,8-DMTHN 97.2%, 1,6-+1,7-DMTHN 0.8%,
1,5-DMN 0.2%, 1,6-DMN 0%,
low boiling light components 1.8%

|  | Comparative Example 5 | Comparative Example 6 |
|---|---|---|
| Catalyst | 1% Re/activated carbon | 1% Ru/activated carbon |
| Liquid feed time (hr) | 22 | 82 | 31 | 63 |
| Temperature (°C.) | 280 | 300 | 280 | 300 |
| DMN yield (%) | | | | |
| 1,5-DMN | 65.1 | 63.4 | 33.4 | 34.8 |
| 1,6-+1,7-DMN | 0.6 | 2.4 | 0.4 | 2.7 |
| 1,8-DMN | 0.2 | 0.1 | 0.1 | 0.0 |
| Conversion efficiency (%) | 68.1 | 71.6 | 34.5 | 40.2 |
| Selectivity to DMN (%) | 96.8 | 92.1 | 98.3 | 93.4 |

What is claimed is:

1. A process for producing dimethylnaphthalene comprising dehydrogenating dimethyl-tetrahydronaphthalene in a gaseous state at a temperature of 200° to 350° C. in the presence of a diluting medium and at least one metallic catalyst selected from the group consisting of platinum and palladium, said catalyst being supported on activated carbon.

2. The process according to claim 1 wherein the diluting medium is at least one inert gas selected from the group consisting of nitrogen, argon and helium.

3. The process according to claim 1 wherein the diluting medium is at least one member selected from the group consisting of aliphatic hydrocarbons and aromatic hydrocarbons, said diluting medium being in a gaseous state under dehydrogenation reaction conditions.

4. The process according to claim 3 wherein the diluting medium is a paraffin having 1 to 15 carbon atoms and a boiling point lower than the boiling point of dimethylnaphthalene.

5. The process according to claim 3 wherein the diluting medium is an aromatic hydrocarbon which is in the form of a liquid at room temperature and having a boiling point lower than the boiling point of dimethylnaphthalene.

6. The process according to claim 1 wherein the diluting medium is in an amount of 0.1 to 100 in a molar ratio based on the dimethyl-tetrahydronaphthalene as a starting raw material.

7. The process according to claim 1 wherein the reaction temperature is 240° to 300° C.

8. The process according to claim 1 wherein the dehydrogenating is carried out at a reaction pressure of 0.1 to 10 atm in terms of absolute pressure.

9. The process according to claim 1 wherein the catalyst is in an amount of 0.05% to 15% by weight based on the activated carbon as a carrier.

10. The process according to claim 1 wherein the dimethyl-tetrahydronaphthalene is introduced at a feed rate as a starting raw material of 0.1 to 10 times by weight per hour based on the unit weight of the catalyst.

11. The process according to claim 1 wherein the dimethyl-tetrahydronaphthalene as a starting raw material is brought into contact with a catalyst by the fixed-bed reaction system.

12. The process according to claim 1 wherein the diluting medium is a linear or branched paraffin having 6 to 10 carbon atoms.

13. The process according to claim 1 wherein the diluting medium is selected from the group consisting of benzene, toluene, o-xylene, m-xylene, p-xylene, ethylbenzene, pseudocumene, mesitylene, n-propylbenzene and cumene.

14. The process according to claim 1 wherein the diluting medium is in an amount of 0.5 to 20 in a molar ratio based on the dimethyl-tetrahydronaphthalene as a starting raw material; the dehydrogenating is carried out at a reaction pressure of 0.5 to 3 atm in terms of absolute pressure; the dimethyl-tetrahydronaphthalene is introduced at a feed rate as a starting raw material of 0.2 to 5 times by weight per hour based on the unit weight of the catalyst; and the catalyst is in an amount of 0.05 to 15 weight % based on the activated carbon weight.

15. The process according to claim 14 wherein the diluting medium is selected from the group consisting of nitrogen, argon, helium, a paraffin having 6 to 10 carbon atoms and having a boiling point lower than the boiling point of dimethylnaphthalene, benzene, toluene, o-xylene, m-xylene, p-xylene, ethylbenzene, pseudocumene, mesitylene, n-propylbenzene and cumene.

16. The process according to claim 15 wherein the reaction temperature is 240° to 300° C.

17. The process according to claim 16 wherein the dimethyl-tetrahydronaphthalene comprises 1,5-dimethyltetralin.

18. The process according to claim 1 wherein the dimethyl-tetrahydronaphthalene is not 1,1-dimethyl-tetrahydronaphthalene or 2,2-dimethyl-tetrahydronaphthalene.

19. The process according to claim 1 wherein the dimethyl-tetrahydronaphthalene is selected from the group consisting of at least one of 1,5-dimethyl-tetrahydronaphthalene, 1,8-dimethyl-tetrahydronaphthalene, 1,6-dimethyl-tetrahydronaphthalene and 1,7-dimethyl-tetrahydronaphthalene.

20. The process according to claim 1 wherein the process is carried out in a reaction mixture consisting essentially of said dimethyl-tetrahydronaphthalene; a diluting medium being selected from the group consisting of nitrogen, argon, helium, a paraffin having 6 to 10 carbon atoms and having a boiling point lower than the boiling point of dimethylnaphthalene, benzene, toluene, o-xylene, m-xylene, p-xylene, ethylbenzene, pseudocumene, mesitylene, n-propylbenzene and cumene; and said metallic catalyst being selected from the group consisting of platinum and palladium, wherein said catalyst being supported on activated carbon.

* * * * *